United States Patent [19]

Loh

[11] Patent Number: 5,686,897
[45] Date of Patent: Nov. 11, 1997

[54] SELF-TESTING ELECTRONIC GROUNDING DEVICE

[76] Inventor: Meow Yew (Philip) Loh, 1993 Vinehill Cir., Fremont, Calif. 94539

[21] Appl. No.: 448,035

[22] Filed: May 23, 1995

[51] Int. Cl.$^6$ .................................................. G08B 21/00
[52] U.S. Cl. .................... 340/649; 340/652; 361/220; 324/509
[58] Field of Search ........................ 340/649, 652, 340/679; 361/42, 220; 324/509–511

[56] References Cited

U.S. PATENT DOCUMENTS

| | | | |
|---|---|---|---|
| 4,373,175 | 2/1983 | Mykkanen | 361/220 |
| 4,577,256 | 3/1986 | Breidagem | 361/220 |
| 4,605,984 | 8/1986 | Fiedler | 361/220 |
| 4,638,399 | 1/1987 | Maroney et al. | 361/220 |
| 4,639,825 | 1/1987 | Breidegam | 361/212 |
| 4,662,695 | 5/1987 | Gordon et al. | 339/14 R |
| 4,736,157 | 4/1988 | Betker et al. | 324/511 |
| 4,745,519 | 5/1988 | Breidegam | 361/220 |
| 4,847,729 | 7/1989 | Hee | 361/220 |
| 4,859,992 | 8/1989 | Hoigaard | 340/649 |
| 4,875,294 | 10/1989 | Campbell | 340/649 |
| 5,004,425 | 4/1991 | Hee | 439/37 |
| 5,018,044 | 5/1991 | Weiss | 361/220 |
| 5,179,497 | 1/1993 | Bakhoum | 361/212 |
| 5,184,274 | 2/1993 | Weiss | 361/220 |
| 5,196,985 | 3/1993 | Ford et al. | 361/220 |
| 5,247,420 | 9/1993 | Bakhoum | 361/212 |
| 5,519,384 | 5/1996 | Chanudet et al. | 340/649 |

*Primary Examiner*—Brent A. Swarthout
*Assistant Examiner*—Daniel J. Wu
*Attorney, Agent, or Firm*—James J. Leary

[57] ABSTRACT

A self-testing electronic personnel grounding device (wrist strap) for the purpose of dissipating static electricity from an individual. It uses a built-in electronic circuitry to detect a break in the electrical continuity in the wrist strap and alerts the wearer when there is a break in electrical continuity owing to broken connections along the dual wire coil cord or at the adjustable elastic wrist band, when it is improperly worn, or when the wearer's body resistance is too high. This device operates on a watch (Nickel-Cadmium, NiCd) type battery to provide the energy source to light an LED (Light emitting Diode) to indicate that there is a break in electrical continuity. The electronic circuitry is designed such that if the wrist band is improperly worn, causing ineffective contact between the human skin and the conductive side of the wrist band, the LED indicator will come on signaling a break in electrical continuity. The circuitry was also designed to be foolproof and also to conserve battery power to last for over one year of normal use and to allow the LED to dim off to alert the user that the battery is running out. This self-testing circuitry uses a dual wire coil cord to provide a closed loop electronic circuit.

19 Claims, 4 Drawing Sheets

SELF-TESTING ELECTRONIC GROUNDING DEVICE

FIELD OF INVENTION

The present invention relates to personnel grounding devices for the removal of static electricity from a human body. More particularly, this invention pertains to a personnel grounding device with a built in electronic circuitry to detect any break in electrical continuity and to alert the wearer.

BACKGROUND OF THE INVENTION

Static electricity has been attributed as the cause of field failure of electronic components which became marginally damaged during the manufacturing process when the personnel handling these components were not effectively grounded. The static electricity sensitive devices like MOS devices could be damaged by static electricity potentials of as little as 50 volts. A person walking on an unprotected carpet in a dry atmospheric condition may generate up to 30,000 volts of static electricity. Hence, if this static electricity is not effectively conducted away from the static electricity sensitive devices, major loss in property may result due to premature or unanticipated failure in these electronic components which may be used to operate computer equipment in man carrying transportation systems like aircraft, space shuttles and the like.

The electronic component and equipment manufacturing industries have implemented various static electricity control measures, one of the most common of which is using personnel grounding wrist straps to drain the static electricity from the bodies of the workers when they are handling such components or equipment. This wrist strap is comprised of an electrically conducting wrist band attached to a grounding cord which in turn connects to the effective earth ground to drain the static electricity from the body.

Over the years a number of inventors have invented different kinds of human grounding wrist straps using a variety of wrist band materials to achieve the goal of discharging static electricity. Those inventions are composed of a wrist band that is made of a conductive material (woven materials, knit materials, metal, conductive plastic material, conductive Velcro™ materials, etc.) to be attached to a single wire cord using a megohm resistor for effective grounding. There were also testing meters for off-site testing for electrical continuity of the wrist strap.

For example U.S. Pat. No. 5,184,274 to Weiss discloses a wrist strap with a detachable plug.

U.S. Pat. No. 4,745,519 to Breidegam discloses a wrist strap with a visual LED signal incorporated into the wrist band. However, the circuit which activates the light is in a module separate from the wrist band. Breidegam suggests miniaturizing the circuit for mounting in the wrist band. However, his circuit is sufficiently large that it is not obvious from his description how this would be accomplished. In any event, Breidegam makes no provisions for disconnecting the battery when the strap is removed from the wrist However, there has been disclosed no invention characterized by simple construction that has the capability to: (a) ensure constant electrical continuity while the wrist cord is worn (b) alert the wearer when there is a break in the continuity (c) disconnect power to the signaling circuit for the purpose of conserving battery power when the device is not in use, and (d) inform the wearer that the wearer's grounding resistance is too high and that the wearer needs to do something to render the grounding effective.

SUMMARY OF THE INVENTION

It is therefore an object of this invention to provide a band to be worn on the wrist that presents in a convenient location (the wrist) a warning that his body is charged with static electricity that could damage components that he is handling.

It is another object that the device be entirely self contained on the wrist in order to avoid the inconvenience arising from separating the parts of the device.

It is another object that the device be constructed such that the battery operating the device be disconnected when the device is not in use.

The present invention is directed toward a wrist strap with a connection to ground and is provided with an electronic means for signaling to the user when electrical continuity has been interrupted. In one embodiment, the signal is a buzzer or vibration, in another embodiment the signal is a light. The ends of the strap are secured around the wrist by a buckle which is also a housing for the battery and circuit that energizes the alarm. When the plug is disconnected from the device, the battery is automatically disconnected thereby conserving the life of the battery.

The present invention revolutionizes the prior art by integrating sophisticated electronic technology into the personnel grounding wrist strap to guarantee electrical continuity, at the same time indicate to the user that there is a break in continuity instantaneously when a break happens. This indication can take the form of a LED (Light Emitting Diode) or a buzzer sound or a vibration medium could be used.

This invention is comprised of a "brain", which is embodied in a buckle-shaped package; a wrist band material that is conductive on the inner side of the band where it is in contact with the human hand and insulative on the outer side of the wrist band, and a dual wire coil cord, terminated at one end to a banana plug and the other end split into two wires, with one wire connected to a one megohm resistor and each then connected to a female anti-fishhooking crimp terminal.

The "brain" is a buckle-shaped device made up of two pieces of plastic which are hinged at one end with metal plates embedded in the bottom plastic piece for effective electrical contact. This buckle houses an electronic circuit board with an LED indicator and a battery. The conductive wrist band is fixed at one end of the buckle making electrical contact, forming part of the electronic circuitry while the other end passes under the top cover making another point of electrical contact in the electronic circuitry to provide an electrical closed-loop band to be worn around a human wrist. Hence, if the band is not making effective electrical contact with the skin, the electronic circuit will work to illuminate the LED. The electronic circuit operates on a wrist watch-type NiCd battery that was selected to last for up to two years of use under normal operating condition in this device. The electronic circuit is designed in such a way that when the top cover is opened, it causes the circuit to be inactive, hence conserving the battery power. The electronic circuit was also designed to cause the LED to dim off when the battery power is running out. The top cover is locked into position to the bottom cover of the buckle by means of a slot and key feature. The key when depressed, separates it from the slot of the key, hence allowing the top cover to be separated from the bottom cover.

The dual wire coiled cord is made of two separate wires, each consisting of sufficient strands of tinsel wires for the purpose of conducting static electricity away from the user.

Preferably, the wires are arranged coaxially with each wire insulated with polyurethane. The final wire assembly is insulated with fire-retarding polyurethane. One end of the cord has the two sets of wires twisted together and terminated to a banana plug or, alternatively, a pair of alligator clips, a BNC connector, or other known electrical connector to connect to ground. At the other end of the coil cord, both wires are connected to a 4809 series anti-fishhooking crimp terminal. A 1 megohm resistor is connected in series with one of the wires at either end of the cord. The end assembly is then molded together to form a plug in PVC material.

With the terminated end of the dual wire coiled cord connected to earth's ground and the female plug end plugged into the buckle connector (which is comprised of two right angle pins connected to the printed circuit board) and the top-cover of the buckle closed, the circuit becomes active and the LED will come on indicating a break in the circuitry. With the wrist band properly worn on the hand and the metal plate at the base of the buckle coming into effective contact with the human hand, the LED will go off immediately, indicating the electrical loop is closed and that there is no break in continuity anywhere.

DETAILED DESCRIPTION OF THE INVENTION

Figure 1:
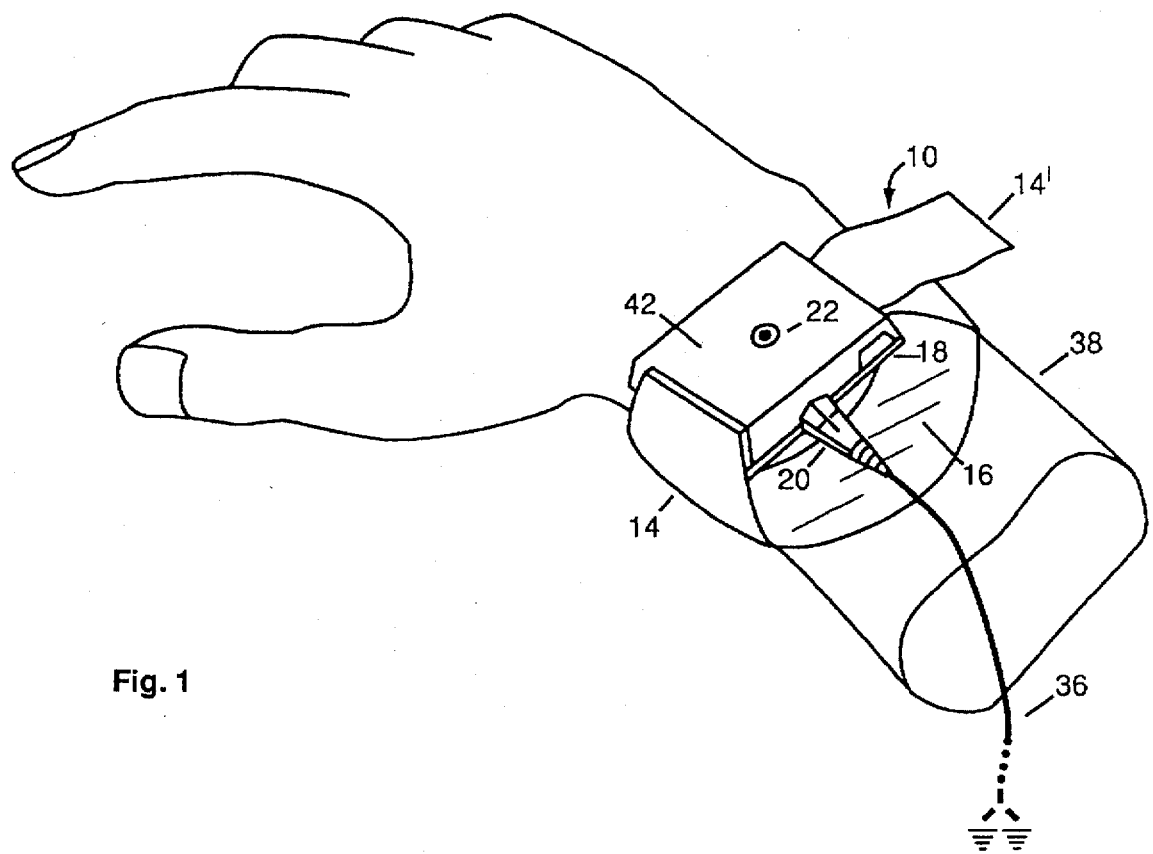
FIG. 1 shows an assembly drawing of the self-testing grounding device of the present invention worn around a user's wrist.

Turning now to a discussion of the drawings, FIG. 1 is an assembly view of the self-testing electronic grounding device of the present invention. The grounding device, which is indicated by reference number 10, is shown attached to the wrist 38 of a user. The electronic circuit 12 (shown schematically in FIG. 3) of the grounding device 10 is contained within a housing unit 42 which attaches to the wrist 38 with a conductive wrist band 14 that has a conductive inner surface 16 surrounding the wrist 38. The conductive wrist band 14 may have one of several known constructions. In one preferred embodiment, the conductive wrist band 14 is a braided elastic strap having wires or conductive fibers braided into the fabric of the strap 14 to form the conductive inner surface 16. Alternatively, the conductive wrist band 14 may have a composite construction with an outer insulating layer 14 laminated to a conductive inner layer 16 which is positioned against the skin of the user's wrist 38

Figure 3:
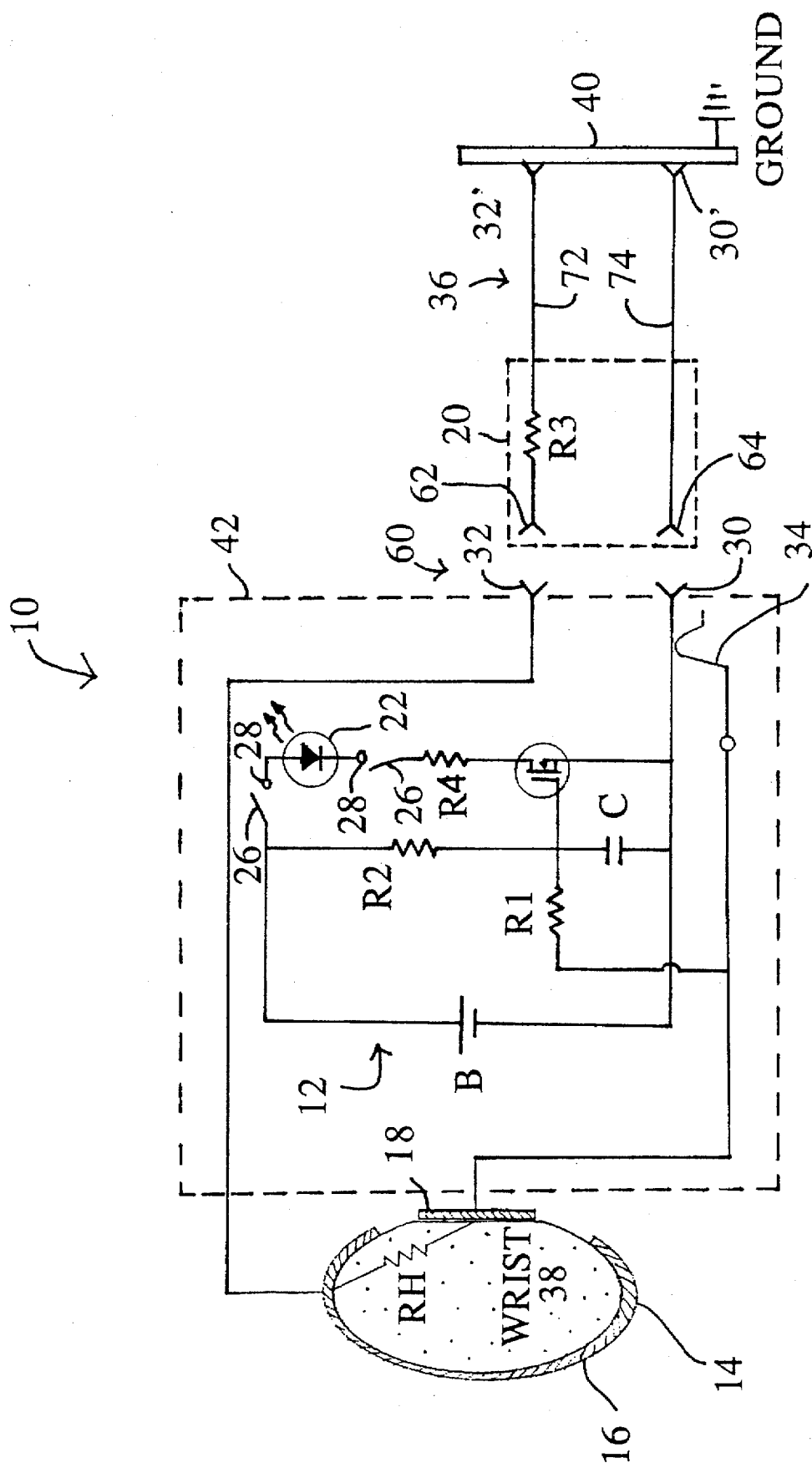
FIG. 3 shows a schematic diagram of the circuit of the self-testing grounding device.

The conductive inner surface 16 of the conductive wrist band 14 forms a first electrical connection with the wrist 38 of the user. A second electrical connection with the wrist 38 is formed by a metal plate 18 which is mounted on the bottom surface of the housing unit 42. The conductive inner surface 16 and the metal plate 18 are electrically connected to one another through two separate paths. One path is through the resistance of the user's wrist RH, and the other path is through the electronic circuit 12 mounted on a printed circuit board within the housing unit 42 and through the ground cable 36, as shown in FIG. 3. The wrist resistance RH is the term used here for the effective resistance between the inner conductive surface 16 of elastic band 14, and metal plate 18. Typical wrist resistance should be less than 10 megohms between the inner conductive surface 16 and the metal plate 18 if the conductive wrist band 14 is tight enough to insure that both the plate 18 and conductive inner surface 16 make good contact with the skin. This figure for the acceptable level of wrist resistance RH is arrived at empirically.

It should be noted that other geometries are possible for the first and second electrical connections with the user provided by the metal plate 18 and the inner surface 16 of the wrist band 14. The grounding device 10 will work with almost any geometry as long as it has at least two conductive surfaces in contact with the user's skin. For example, the conductive wrist band 14 could be made with two regions of conductive material separated by an insulating section. The two conductive regions could be arranged as parallel bands of conductive skin contacts along the inner surface of the wrist band 14 or they could be arranged as patches of conductive skin contacts separated along the length of the wrist band 14

Figure 2:
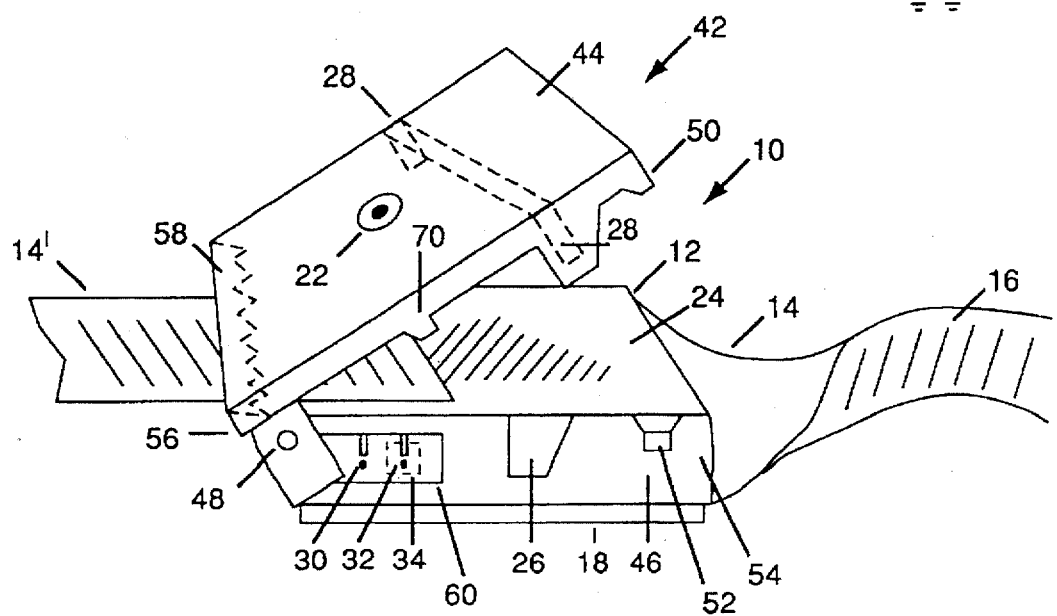
FIG. 2 shows a detailed view of the self-testing grounding device with the housing unit opened to show the interior.

Besides serving as an enclosure for the electronic circuit 12 (not visible beneath the insulating surface 24) of the grounding device 10, the housing unit 42, shown in greater detail in FIG. 2, also serves as a buckle or clasp for the conductive wrist band 14. The housing unit 42 has an upper section 44 which is pivotally attached to a lower section 46 by a pair of hinges 48. The upper 44 and lower 46 sections of the housing unit 42 are preferably injection molded of an antistatic plastic material. The end 14' of the conductive wrist band 14 is passed around the wrist and inserted into the housing unit 42 through a slot 56 between the upper section 44 and the lower section 46, then pulled tight. When the housing unit 42 is closed, a row of teeth 58 molded into the upper section 44 grasps the conductive wrist band 14 against an insulating surface 24 within the lower section 46 and holds it tight around the user's wrist. A pair of catches 50 on the upper section 44 engage a pair of corresponding recesses 52 on the lower section 46 and hold the housing unit 42 closed. To open the housing unit 42 and release the conductive wrist band 14, the user squeezes on a pair of flexible ears 54 on the sides of the lower section 46 to disengage the recesses 52 from the catches 50 and lifts up on the edge of the upper section 44.

A light emitting diode (LED) 22 is mounted within the upper section 44 of the housing unit 42 so that it is visible to the user through an opening in the upper section 44. The LED 22 lights up to alert the user when the detection circuit 12 senses a fault in the grounding of the device 10. If desired, other types of alerting devices may be used in conjunction with or in place of the LED 22, for example a buzzer or a vibratory device could be used to give the user an audible or tactile signal that a fault in the grounding of the device 10 has been detected.

The housing unit 42 also serves as a battery conservation switch to disconnect the battery from the detection circuit 12 when the grounding device 10 is not in use. A pair of electrical contacts 28 within the upper section 44 engage a pair of corresponding electrical contacts 26 within the lower section 46 when the housing unit is closed. When the housing unit 42 is opened by lifting the upper section 44, the upper contacts 28 disengage the lower contacts 26, thereby disconnecting the LED 22 from the remainder of the electronic circuit 12. Access to the circuit 12 and battery B are also gained through insulating surface 24, which pops out of the lower section 46 of the housing unit 42.

Figure 4:
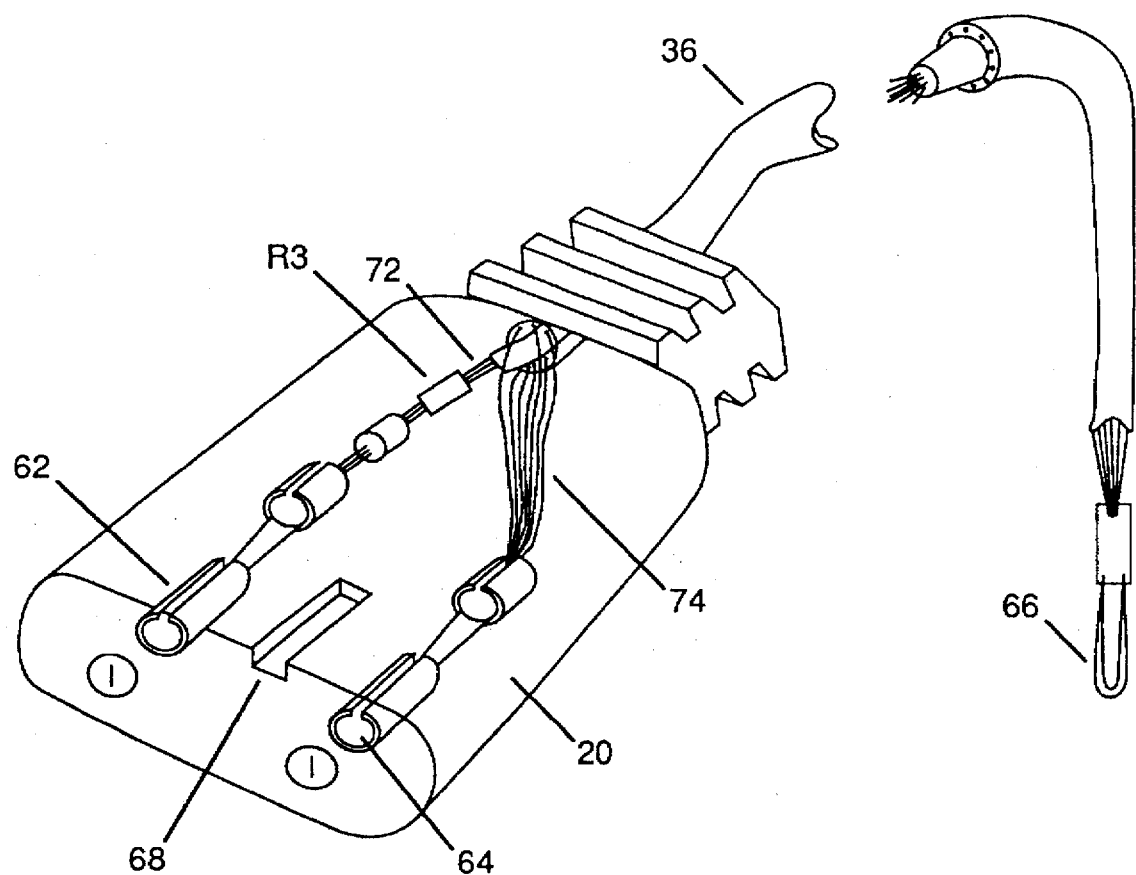
FIG. 4 shows a detailed view of the connector plug and the grounding cable of the self-testing grounding device.

The lower section 46 of the housing unit 42 has an electrical connector 60 which includes a first terminal 30 and a second terminal 32, which are connected to ground through a grounding cable 36 that has a connector plug 20 which plugs into the electrical connector (see FIG. 1). The grounding cable 36 and the connector plug 20 are shown in greater detail in FIG. 4. The connector plug 20 is a molded plastic connector. A keyway 68 in the connector plug 20 aligns with a tab 70 in the electrical connector 60 of the housing unit 42 to ensure that the connector plug 20 is properly connected. A first female connector 62 and a second female connector 64 are enclosed within the connector plug 20. The first female connector 62 connects to a first conductor 72 in the grounding cable 36 through a one megohm resistor R3. The second female connector 30 of the connector plug 20 connects to a second conductor 72 in the grounding cable 36. The first 72 and second 74 conductors are each insulated within the grounding cable 36. Preferably, the first 72 and second 74 conductors are coaxially arranged within the grounding cable 36. Alternatively, the first 72 and second 74 conductors can be arranged as a twisted pair or a parallel pair within the grounding cable 36. The other ends of the first 72 and second 74 conductors are terminated in a male banana plug 66 to connect to ground. The conductive wrist band 14 is connected to ground 40 via terminal 32 and first conductor 72. The detector circuit 12 is connected to ground 40 via terminal 30 and second conductor 74. Alternatively, a pair of alligator clips 30', 32' can be provided in place of the banana plug 66 to connect the first 72 and second 74 conductors individually to ground 40, as shown schematically in FIG. 3. Other types of electrical connectors such as a BNC connector, or other known electrical connectors may be also be used in place of the banana plug 66.

The electrical connector 60 also contains a battery conserving switch 34 which is activated by removal of the connector plug 20 from the housing unit 42. Removing the plug 20 from the electrical connector 60 will prevent the LED 22 from turning on and draining the battery when the grounding device 10 is not in use. The battery conserving switch 34 is more fully discussed below in connection with FIG. 3 and FIG. 5.

The entire circuit configuration of the self-testing grounding device 10 is shown schematically in FIG. 3. During normal operation, LED 22 is off. The contacts to ground 30' and 32' that correspond to the terminals 30 and 32 on circuit unit 12 are connected to the ground wire 40. Switch 34 is disconnected when the connector plug 20 is inserted to connect terminals 30 and 32 to the corresponding female connectors 62 and 64 in connector plug 20 of the ground cable 36. If wristband 10 is making contact to the user's wrist through both wrist plate 18 and conductive strap 14, then the gate of the FET is also basically at ground, because resistor R2 has such a large resistance compared to resistor R1, and capacitor C is at ground also, since connection 32' is grounded. The FET is off, and, in turn, so is device 22.

Also, it is the large resistance of R2 that enables the battery to last such a long time. If everything is properly connected, there is still a small trickle of current through R2, R1, the wrist resistance, across to the wrist to strap 14, and finally to ground through resistor R3. But it is the large resistance of R2, as well as the small battery voltage that enables the battery to last up to two years.

There are three basic conditions that will trigger the warning device 22:

1) The grounding device 10 is loose around the wrist so that either the metal plate 18 or the inner conductive surface 16 of the conductive wrist band are not in proper electrical contact with the wrist.
2) Either, or both, of connectors 30' or 32' are loose, or not connected to the ground wire 40.
3) The wearer's body resistance is greater than 10 megohm.

If one of the above occurs, LED 22 will turn on allowing a current through resistor R4, which is a standard drain resistor for a FET carrying a load, i.e. the voltage drop across it should be appropriate to limit the battery current to the FET and LED 22 warning device.

Considering the two possible triggering mechanisms for LED 22 warning device, both rely on the positive biasing of the gate of the FET with respect to the source/base connection with the battery voltage. If either of the ground connections 30'32' are suspect, or if grounding device 10 is loose, and the wrist resistance RH becomes too great, the connections to ground are interrupted, the battery will charge capacitor C to positively bias the line running to the FET's gate, and turn it on. In turn, LED 22 is triggered.

Both R1 and R3 also serve to protect the user in case there is some sort of voltage transient or noise in the ground line. R3 protects the user from unexpected wristband voltage coming from connection 30', and R1 protects against unexpected voltage from connection 32' that would be transmitted through the capacitor, and would have the opposite polarity on the user's wrist, setting up a potential difference and a possible large current path between plate 18 and strap 14.

In a preferred embodiment, grounding device 10 uses a 3 volt battery B. The FET will have a threshold voltage of between 0.5 volts and 1.5 volts, but preferably around 1 volt. R1 and R3 are both 1 megohm resistors. R2 is the large resistor with a 40 megohm resistance. R4 depends upon warning device 22 and the FET, and may be suitably chosen by one skilled in the art. The above resistances are appropriate values if a light emitting diode 22 is used as the warning device. Modifications may be needed to the circuit 12 for use with buzzers, vibrators or other types of warning devices.

The electrical connection of the grounding cable 36 with the detection circuit 12 is shown schematically in FIG. 3. The connector plug 20 on the end of ground cable 36 contains the safety resistor R3 which was also seen in FIG. 4. Safety resistor R3 is between the ground wire and terminal 30, and as such this resistor is not part of circuit 12, but rather part of grounding cable 36. The schematic diagram in FIG. 3 indicates the switch 34 that shorts terminal 32 to wrist plate 18 when the connector plug 20 is removed from the electrical connector 60 in the housing unit 42. If the connector plug 20 on grounding cable 36 is pulled out of circuit 12, that has the same effect as disconnecting connections 30' and 32' (although the disconnection occurs at the plug 20 end of the grounding cable 36), and switch 34 makes a connection and the connections to ground disappear. Again, there is a trickle of current, but this time on a different path. Current will travel from the anode of the battery to the cathode through R1 and R2 when cord 20 is unplugged. Again, R2 is large enough to limit the current, and the battery lasts about the same amount of time as a watch battery.

Figure 5:
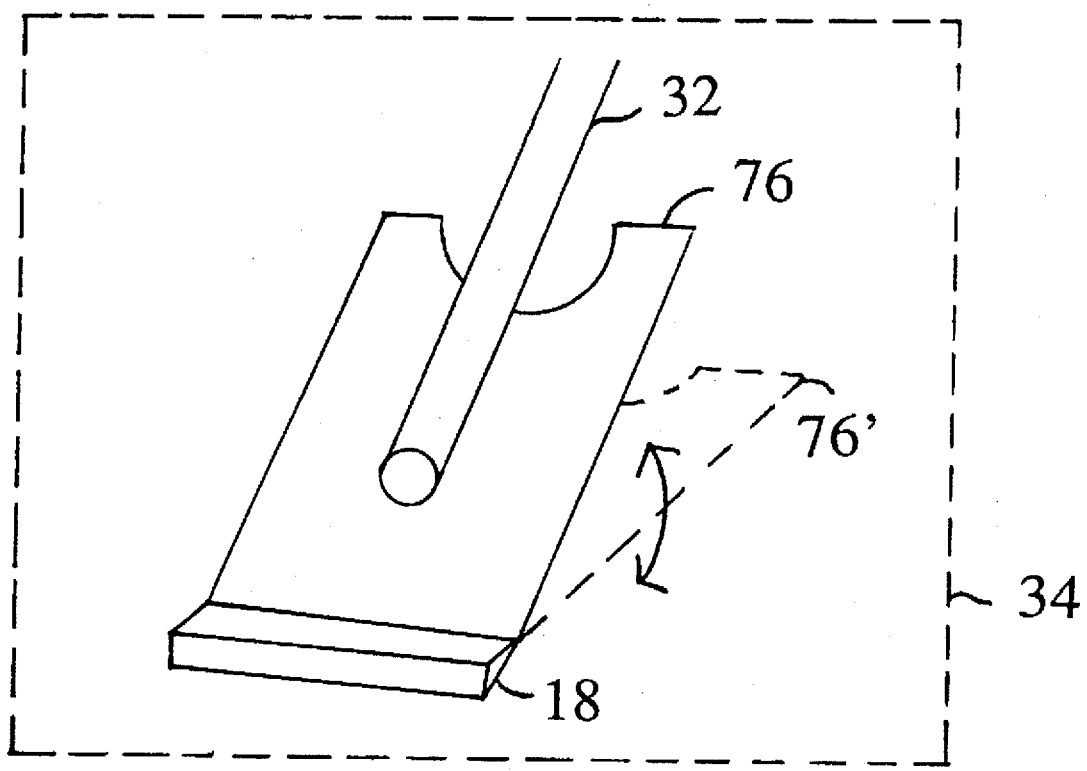
FIG. 5 shows a detailed view of the connector plug-responsive battery conserving switch.

FIG. 5 more clearly illustrates the design of switch 34. It is simple and cheap, but clever in that it does not simply turn a circuit off, but rather it changes the micro-current flow on grounding device 10 from one circuit to another. The spring contact 76 is electrically and mechanically connected to wrist plate 18. When the connector plug 20 at the end of grounding cable 36 is inserted into the electrical connector 60 of circuit unit 12, it physically moves the contact 76 down and away from terminal 32 to position 76', and the self-testing grounding device 10 is again active to detect whether the user is grounded. When the connector plug 20 is removed, the contact 76 springs up, shorts the source of the FET to the gate via wrist plate 18 and terminal 32, and the warning device 22 will not turn on. The user may then leave the work bench with grounding device 10 on, and the warning device 22 will not drain the battery B.

It should be noted that if one wants to turn the battery off completely, terminals 30 and 32 should be disconnected (leaving cord 20 plugged into circuit unit 12), and the top of circuit unit should be popped open.

A major feature of the invention is the simplicity of construction for achieving the objects of the invention which are to provide a device that can be worn conveniently with the alert signal in constant field of view and wherein power to the battery is immediately disconnected when the plug is removed from the device.

Other embodiments may be contemplated which are within the scope of the invention. For example, the construction may incorporate "hook and eye" material (Velcro™) in place of a buckle in which the printed circuit board and battery are attached to one end of the strap and the battery has a lead going through a conducting portion of the strap which becomes separated from the section containing the battery so as to disconnect the battery when the device is separated from the wrist. An audible buzzer may be used in placed of the LED.

Although the invention has been described with reference to specific embodiments, this description is not meant to be construed in a limiting sense as various other embodiments are contemplated and that numerous additions, modifications and alterations may be made to the embodiment shown. For example, to alert the wearer of a break in continuity could come in different forms, e.g. instead of using a colored LED, it could be a sound emitter in the form of a beeper or buzzer, or a vibrator type device. With the advancements of energy storage technology, the battery may be replaced by a solar cell. It is therefore contemplated that the appended claims will cover such modifications that fall within the true scope of the invention.

I claim:

1. A self-testing grounding device comprising:
   a conductive strap physically attached to a circuit unit to form a wristband;
   a conductive cord with one end electrically connected to said circuit unit with a removable plug, and the other end electrically connected to a voltage potential, wherein;
   said circuit unit has an internal power supply, and also an external warning device that will turn on if said wristband becomes disconnected to said voltage potential,
   wherein said conductive strap and said circuit unit are electrically separated by a variable electrical resistance,
   wherein said conductive cord comprises two parallel wires, respectively connected to said conductive strap and said circuit unit on one end, and to said common voltage potential on the other end, wherein, of each of said two parallel wires, one is connected to a gate of a field effect transistor through said variable resistance and through a conductive plate located on said circuit unit, and the other is connected to the source and base of said field effect transistor.

2. The self-testing grounding device of claim 1 wherein said variable resistance arises from electrical current from said internal power supply traveling through part of a wrist.

3. The self-testing grounding device of claim 1 wherein resistors exist in said circuit unit and said conductive cord and said resistors protect a wrist from variations in said voltage potential.

4. The self-testing grounding device of claim 1 wherein said circuit unit is battery powered.

5. The self-testing grounding device of claim 1 wherein said circuit unit is powered by a solar cell.

6. A self-testing grounding device comprising:
   a conductive strap physically attached to a circuit unit to form a wristband;
   a conductive cord with one end electrically connected to said circuit unit with a removable plug, and the other end electrically connected to a voltage potential, wherein;
   said circuit unit has an internal power supply, and also an external warning device that will turn on if said wristband becomes disconnected to said voltage potential,
   wherein disconnection of said removable plug from said circuit unit actuates a switch to convert said circuit unit to a power saving mode.

7. The self-testing grounding device of claim 6 wherein said circuit unit is battery powered.

8. The self-testing grounding device of claim 6 wherein said circuit unit is powered by a solar cell.

9. A self-testing grounding device comprising:
   a conductive strap physically attached to a circuit unit to form a wristband;
   a conductive cord with one end electrically connected to said circuit unit with a removable plug, and the other end electrically connected to a voltage potential, wherein;
   said circuit unit has an internal power supply, and also an external warning device that will turn on if said wristband becomes disconnected to said voltage potential,
   wherein said circuit unit resides within a housing having a closure means, and wherein opening said closure means actuates a switch to convert said circuit unit to a power saving mode.

10. The self-testing grounding device of claim 9 wherein said circuit unit is battery powered.

11. The self-testing grounding device of claim 9 wherein said circuit unit is powered by a solar cell.

12. A self-testing grounding device for grounding the body of a user, said device comprising:
    a first contact means for electrically connecting to the body of said user,
    a second contact means for electrically connecting to the body of said user,
    means for connecting said first contact means and said second contact means to ground,
    circuit means for testing an electrical resistance of a conductive pathway between said first contact means and said second contact means through the body of said user and for activating a warning means if said resistance is greater than a predetermined value,
    and a switch means for switching said circuit means to a power saving mode.

13. The self-testing grounding device of claim 12 wherein said first contact means comprises a conductive wrist strap.

14. The self-testing grounding device of claim 12 wherein said first contact means comprises a conductive plate in contact with a wrist of the user.

15. The self-testing grounding device of claim 12 wherein said circuit means includes an internal power supply.

16. The self-testing grounding device of claim 12 wherein said circuit means is powered by a solar cell.

17. The self-testing grounding device of claim 12 wherein said warning means comprises a light emitting diode.

18. The self-testing grounding device of claim 13 wherein said warning means comprises an audible buzzer.

19. The self-testing grounding device of claim 12 wherein said circuit unit is battery powered.

* * * * *